United States Patent
Wang et al.

(10) Patent No.: US 7,312,368 B2
(45) Date of Patent: Dec. 25, 2007

(54) METHOD FOR SELECTIVE REDUCTION OF AROMATIC COMPOUNDS

(75) Inventors: Peter Xianqi Wang, Chesterfield, MO (US); Frank W. Moser, Arnold, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 57 days.

(21) Appl. No.: 10/581,418

(22) PCT Filed: Dec. 2, 2004

(86) PCT No.: PCT/US2004/040243

§ 371 (c)(1), (2), (4) Date: Jun. 2, 2006

(87) PCT Pub. No.: WO2005/068403

PCT Pub. Date: Jul. 28, 2005

(65) Prior Publication Data

US 2007/0112232 A1    May 17, 2007

(51) Int. Cl.
*C07C 17/10* (2006.01)

(52) U.S. Cl. ............... 570/230; 568/717; 568/774; 564/161; 564/170; 564/171; 564/305

(58) Field of Classification Search ............... None
See application file for complete search history.

(56) References Cited

OTHER PUBLICATIONS

Birch, Reduction by Dissolving Metals. Part I., Chem. Soc. 1944, pp. 430-436.
Birch, The reduction of organic compounds by metal-ammonia solution, Quart. Rev. Chem. Soc. 1950, 4, pp. 69-93.
Radideau, The metal-ammonia reduction of aromatic compounds, Tetrahedron 1989, 45, pp. 1579-1603.
Mander, Partial reduction of aromatic rings by dissolving metals and by other methods, Comprehensive Organis synthesis 1991, 8, pp. 489-521.
Birch, The Birch reduction in organic synthesis, Pure & Appl. Chem. 1996, 68, pp. 553-555.
Alonso et al., The $NiCl_2.2H_2O$-Li-arene combination as reducing system. 4. Dehalogenation of organic halides using the $NiCl_2.2H_2O$-Li-DTBB (cat.) combination, Tetrahedron 1999, 55, pp. 4441-4444.
Berkowitz, An efficient dechlorination method for 1,2,3,4-tetrachloro-5,5-dimethoxcyclopentadiene Diels-Alder adduct: Inverse addition-etheral Birch reduction condition, Synthesis 1990, 8, pp. 649-651.
Bryce-Smith et al., Reduction of organic halides. Chlorobenzene to benzene, Org. Synth 1967, 47, p. 103.
Rossi et al., On the dehydroxylation of phenols by cleavage of their diethyl phosphate esters with alkali methals in liquid ammonia, J. Org. Chem. 1973, 38, p. 2314.
Welch et al., Reduction of aryl diethyl phosphates with titanium metal: a method for deoxygenation of phenols, J. Org. Chem. 1978, 43, p. 4797.
Birch et al., Reaction mechanisms in reductions by metal-ammonia solutions, Tetrahedron 1959, 6, pp. 148-153 XP-002333355.
Kaiser, A Comparison of Methods Using Lithium/Amine and Birch Reduction Systems, Synthesis, Thieme, Stuttgart, DE Aug. 1972, 8, pp. 391-415 XP002046306.
Birch et al., Reductions by metal-ammonia solutions and related reagent, Advanced Organic Chemistry 1972, 8, pp. 1-65 XP009049761.
International Search Report dated Jun. 28, 2005.

*Primary Examiner*—Sikarl A. Witherspoon
(74) *Attorney, Agent, or Firm*—Sarah Pfeifer Vaz; Blackwell Sanders LLP

(57) ABSTRACT

A method for the selective reduction of an aromatic compound. The present invention provides a method for preventing the reduction of at least one halogen substituted aromatic ring of an aromatic compound, while allowing the reduction of at least one functional group on the aromatic compound. In the present invention at least one hydroxyl group is placed on the at least one halogen substituted aromatic ring to be protected from reduction. The aromatic compound is then reacted with at least one alkali metal in at least one nitrogen containing base and at least one alcohol at a ratio of the alcohol to the nitrogen containing base at which the aromatic ring with the hydroxyl group is protected from reduction, while the desired functional group is reduced.

17 Claims, No Drawings

METHOD FOR SELECTIVE REDUCTION OF AROMATIC COMPOUNDS

FIELD OF THE INVENTION

The present invention relates to a method for selectively reducing aromatic compounds, and more specifically a method for selectively retaining a halogen group on an aromatic ring under modified dissolving metal reduction conditions.

BACKGROUND OF THE INVENTION

The dissolving metal reduction reaction, also known as a Birch reduction, is used for reducing compounds, including the reduction of aromatic compounds to 1,3-cyclohexadiene or 1,4-cyclohexadiene and dehalogenation reactions, is well known in the art. Dissolving metal reductions are an important organic synthesis tool. Although run under severe reaction conditions, the reduction has been widely applied in organic synthesis, for example in the partial reduction of an aromatic ring to 1,4-cyclohexadienes or 1,3-cyclohexadienes. Dissolving metal reductions also reduce other functional groups on an aromatic ring or olefin, including the C—X bond, wherein X is a halogen, to C—H.

The dissolving metal reduction comprises reacting with an alkali metal in the presence of a nitrogen containing base, typically ammonia. The alkali metal is typically Li, Na, K or Ca. The reaction takes place in a solvent system, for example alcohols and mixtures thereof. The dissolving metal reduction is typically carried out at a reduced temperature.

Unfortunately, a conventional dissolving metal reduction results not only in reduction of aromatic rings, but also halogens and other reducible functional groups present. Protection of the C—X bond on the halogenated aromatic ring under dissolving metal reduction conditions has not previously been shown. Selective C—X bond retention would greatly broaden the scope of the dissolving metal reduction reaction. It is therefore desirable to provide a method for selectively reducing or dehalogenating an aromatic compound.

SUMMARY OF THE INVENTION

An illustrative aspect of the present invention is a method for the selective reduction of an aromatic compound. The present invention provides a method for preventing the reduction of at least one halogen substituted aromatic ring of an aromatic compound, while allowing the reduction of at least one functional group on the aromatic compound. In the present invention at least one hydroxyl group is placed on the at least one halogen substituted aromatic ring to be protected from reduction. The aromatic compound is then reacted with at least one alkali metal in at least one nitrogen containing base and at least one alcohol, while maintaining a ratio of the alcohol to the nitrogen containing base at which the at least one halogen substituted aromatic ring with the hydroxyl group is protected from reduction, while the desired functional group is reduced.

Another aspect of the present invention is to provide a method for selectively dehalogenating an aromatic compound. The present invention provides a method for preventing the removal of at least one halogen on at least one aromatic ring of an aromatic compound, while allowing the removal of at least one halogen from the aromatic compound. In the present invention at least one hydroxyl group is placed on the at least one aromatic ring on which the halogen to be retained is attached. The aromatic compound is then reacted with at least one alkali metal in at least one nitrogen containing base and maintained at a temperature at which the aromatic ring with the hydroxyl group is protected from dehalogenation, while the desired halogen group is removed from the aromatic compound.

It is understood that these aspects are only provided for the purposes of illustration and are not meant to be limiting of the present invention in any way.

DETAILED DESCRIPTION

There is provided a method for the selective reduction of an aromatic compound. The partial reduction of aromatic rings to 1,3-cyclohexadiene or 1,4-cyclohexadiene typically occurs as a result of a dissolving metal reduction. The inventive method of the present invention allows one or more halogen substituted aromatic rings of an aromatic compound to be protected from reduction. The aromatic rings are protected by the presence of at least one hydroxyl group on the aromatic ring to be protected.

The reaction requires mild reaction conditions for the dissolving metal reduction. The modified metal reduction uses an alkali metal, typically lithium, sodium, potassium, calcium or a mixture thereof as a reductive reagent. The reaction further includes a nitrogen containing base, typically ammonia or a lower amine, and the presence of at least one alcohol. Suitable lower amines include but are not limited to ammonia, methylamine, ethylamine and mixtures thereof. The following solvent/nitrogen bases are particularly well suited for the present invention: a mixture of at least one alcohol and ammonia or at least one lower amine, or at least one alcohol, ammonia or at least one lower amine and at least one organic co-solvent. Suitable organic co-solvents include but are not limited to THF, ether and mixtures thereof. The dissolving metal reduction is carried out at a reduced temperature and at a ratio of nitrogen containing base to alcohol at which the reduction or dehalogenation of the protected aromatic ring is prevented. A presently preferred ratio of alcohol to nitrogen containing base is about 1:1 to about 1:4.

The reaction temperature is typically maintained at about −30° C. or lower. It is believed that the at least one hydroxyl group on the aromatic ring helps to stabilize and protect the ring from reduction, and the C—X bond from dehalogenation under these reaction conditions. The hydroxyl group may optionally be removed after the reduction reaction by any method known in the art.

In an illustrative example, the aromatic compound to be reduced is dissolved in a lower alcohol, for example ethanol, and cooled to a temperature at or below about −30° C. Ammonia gas is then condensed into the reaction vessel under an inert atmosphere, and the reaction is followed by HPLC analysis. When the reaction is substantially complete, the reaction mixture is warmed, neutralized, and diluted with water. The organic compound is extracted, washed and evaporated to yield the product. The recovery processes are all well known in the art.

The present inventive method is particularly useful in organic synthesis involving aromatic compounds having at least one first halogen substituted aromatic ring to be protected, and at least one second aromatic ring to be reduced. The desired reduction may be of the second aromatic ring to a 1,4-cyclohexyldiene or a 1,3-cyclohexyldiene, removal of at least one halogen (dehalogenation), the reduction of another functional group or a combination thereof.

The method involves first protecting each of the at least one first halogen substituted aromatic ring with at least one hydroxyl group. In the synthesis of certain compounds, the intermediate of the desired compound will already include the hydroxyl group. In other compounds, the hydroxyl group will need to be added by any method well known in the art. The second ring of the aromatic compound is then reduced by reacting the compound with at least one alkali metal in the presence of at least one nitrogen containing base and at least one alcohol, wherein the ratio of the alcohol to the nitrogen containing base is such that the at least one first aromatic compound is not reduced. This temperature is typically at or below −30° C. After completion of the selective reduction the hydroxyl group can be removed from the compound if desired.

A selective reduction is seen in the following reaction, wherein the halogen of the aromatic ring is protected by the hydroxyl groups, while the other aromatic ring is reduced to a 1,4-cyclohexadiene:

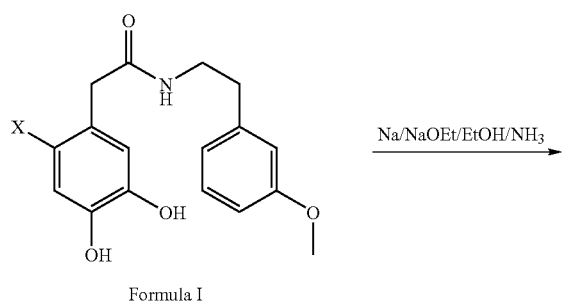

Formula I

Na/NaOEt/EtOH/NH₃

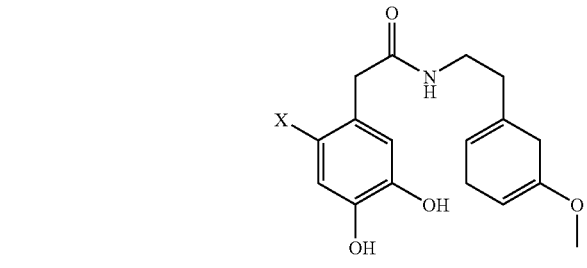

Formula II

A selective dissolving metal reduction is seen in the following reaction, wherein the halogen of the aromatic ring is protected by a hydroxyl group, while the other aromatic ring is dehalogenated:

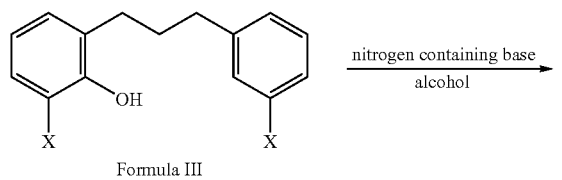

Formula III

Formula IV

The following examples are given for purposes of illustration only and are not meant to limit the present invention in any way.

EXAMPLE 1

Formula I

Na/NaOEt/EtOH/NH₃

Formula II

Formula I (4.50 g, 13.4 mmol) was dissolved in EtOH (125 mL) and cooled to −70 C. Ammonia gas was condensed into the above solution to a volume of 275 mL. NaOEt (5.05 g, 5.5 eq) was added under nitrogen. Sodium metal was cut and added incrementally to the solution. The reaction mixture was sampled periodically over time to follow the progress of the reaction by HPLC. Samples were taken and dissolved in NH₄OAc solution at pH=8.5~9.5. After 3.25 equivalents of sodium were added, more than 95% starting materials were converted to Formula II by HPLC analysis.

The reaction was warmed up to 10° C., neutralized by NH₄Cl/H₂0 to pH=8.5~9.5, diluted with water (300 mL) extracted with ethyl acetate (2×150 mL). The combined organic layers were washed with 5% NH₄OAc (2×250 mL), and water (2×75 mL). The organic layer was pumped down to give 4.18 g of sticky material. Both NMR and HPLC analysis showed that the ratio of the Birch product (Formula VIII) to the dechlorinated side product was 92:8.

EXAMPLE II

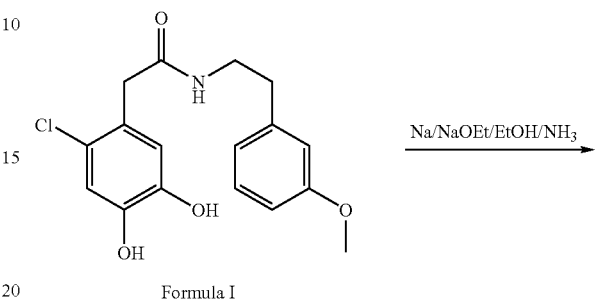

Formula V  Formula VI  Formula VII

Li/LiOBu-t/EtOH/NH₃

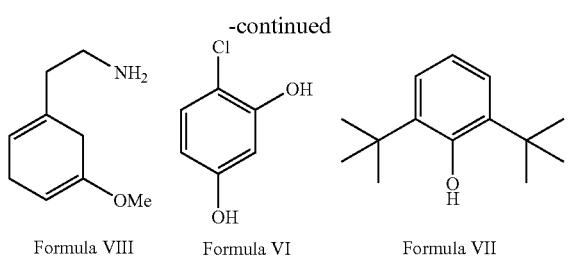

Formula VIII     Formula VI     Formula VII

4-Chlororesorcinol (2.89 g, 20 mmol) and 3-methoxyphenethylamine (3.02 g, 10 mmol) were dissolved in EtOH (50 mL). 2,6-di-t-Butylphenol (0.22 g, 1 mmol) was added as a reference compound. The reaction mixture was cooled to −70° C. Ammonia (gas) was condensed at −70° C. into the cold solution to a final volume of 100 mL. t-BuOK (5.84 g, 32 mmol) was added under nitrogen. Cut lithium metal shavings were added over time to the solution. The reaction mixture was periodically sampled by dissolving small aliquiots in $NH_4Cl/NaH_2PO_4$ solution at pH=8 to 8.5. The progress of the reaction was followed by HPLC. After 2.5 equivalents of Li was added, 98% of the 3-methoxyphenethylamine converted into its Birch reduction product while only 2% of 4-chlororesorcinol dechlorinated according the HPLC analysis.

The invention claimed is:

1. A method for preventing the dehalogenation of an aromatic compound, the method comprising:
protecting an at least one halogen substituted aromatic ring of the aromatic compound with at least one hydroxyl group located on the at least one halogen substituted aromatic ring of the aromatic compound;
reacting the aromatic compound with at least one alkali metal or alkaline earth metal in an at least one nitrogen containing base and at least one alcohol; and
maintaining a ratio of the alcohol to the nitrogen containing base at which the at least one halogen substituted aromatic ring is not dehalogenated.

2. The method of claim 1 wherein the at least one alkali metal or alkaline earth metal includes an alkali metal or alkaline earth metal selected from the group consisting of Li, Na, K, Ca and mixtures thereof.

3. The method of claim 1 wherein the at least one nitrogen containing base includes a base selected from the group of ammonia, methylamine, ethylamine and mixtures thereof.

4. The method of claim 1 wherein the ratio of the alcohol to the nitrogen containing base is about 1:1 to about 1:4.

5. The method of claim 1 further including removing the at least one hydroxyl group from the at least one aromatic ring.

6. A method for the selective reduction of a compound having at least one first aromatic ring including at least one halogen group and at least one second aromatic ring, the method comprising:
protecting the at least one first halogen substituted aromatic ring with at least one hydroxyl group located on the at least one first halogen substituted aromatic ring;
reducing an at least one functional group on the at least one second aromatic ring by reacting the compound with at least one alkali metal or alkaline earth metal in the presence of at least one nitrogen containing base and at least one alcohol; and
maintaining a ratio of the nitrogen containing base to the alcohol, at which the at least one first halogen substituted aromatic ring is not reduced.

7. The method of claim 6 wherein the at least one alkali metal or alkaline earth metal includes an alkali metal or alkaline earth metal selected from the group consisting of Li, Na, K, Ca and mixtures thereof.

8. The method of claim 6 wherein the at least one nitrogen containing base includes a base selected from the group of ammonia, methylamine, ethylamine and mixtures thereof.

9. The method of claim 6 wherein the ratio of the alcohol to the nitrogen containing base is about 1:1 to about 1:4.

10. The method of claim 6 further including removing the at least one hydroxyl group from the at least one aromatic ring after the selective reduction.

11. The method of claim 6 wherein the at least one second aromatic ring is reduced to a 1,3-cyclohexadiene or 1,4-cyclohexadiene.

12. The method of claim 6 wherein the at least one second aromatic ring includes at least one halogen group wherein the at least one second aromatic ring is dehalogenated.

13. A method for selective dehalogenation of an aromatic compound having at least one first aromatic ring including at least one halogen group and at least one second aromatic ring having at least one halogen group, the method comprising:
protecting the at least one first aromatic ring with at least one hydroxyl group located on the at least one first aromatic ring;
dehalogenating the at least one second aromatic ring by reacting the aromatic compound with at least one alkali metal or alkaline earth metal in the presence of at least one nitrogen containing base and at least one alcohol; and
maintaining a ratio of the alcohol to the nitrogen containing base at which the at least one halogen group on the at least one first aromatic ring is retained on the first aromatic ring.

14. The method of claim 13 wherein the at least one alkali metal or alkaline earth metal includes an alkali metal or alkaline earth metal selected from the group consisting of Li, Na, K, Ca and mixtures thereof.

15. The method of claim 13 wherein the at least one nitrogen containing base includes a base selected from the group of ammonia, methylamine, ethylamine and mixtures thereof.

16. The method of claim 13 wherein the ratio of the alcohol to the nitrogen containing base is about 1:1 to about 1:4.

17. The method of claim 13 further including removing the at least one hydroxyl group from the at least one aromatic ring after the selective dehalogenation.

* * * * *